(12) United States Patent
Kissel et al.

(10) Patent No.: US 7,679,058 B2
(45) Date of Patent: Mar. 16, 2010

(54) SYSTEMS AND METHOD FOR PREDICTING THE LIME REQUIREMENT IN SOILS

(75) Inventors: David E. Kissel, Bogart, GA (US); Miguel L. Cabrera, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 296 days.

(21) Appl. No.: 11/792,807

(22) PCT Filed: Dec. 15, 2005

(86) PCT No.: PCT/US2005/045379
§ 371 (c)(1),
(2), (4) Date: Jun. 11, 2007

(87) PCT Pub. No.: WO2006/065970
PCT Pub. Date: Jun. 22, 2006

(65) Prior Publication Data
US 2008/0137069 A1    Jun. 12, 2008

Related U.S. Application Data

(60) Provisional application No. 60/636,784, filed on Dec. 16, 2004.

(51) Int. Cl.
*G01J 5/02* (2006.01)
(52) U.S. Cl. ............... 250/339.07; 250/339.09
(58) Field of Classification Search ........... 250/339.02, 250/339.07, 339.11, 339.12; 436/31, 172
See application file for complete search history.

(56) References Cited

U.S. PATENT DOCUMENTS

| | | | |
|---|---|---|---|
| 4,685,339 A | 8/1987 | Philipenko | 73/864.45 |
| 5,038,040 A | 8/1991 | Funk et al. | 250/341 |
| 5,242,602 A * | 9/1993 | Richardson et al. | 210/745 |
| 5,887,491 A | 3/1999 | Monson et al. | 74/864.74 |
| 6,339,222 B1 * | 1/2002 | Kester et al. | 250/339.09 |
| 6,483,583 B1 | 11/2002 | Wright et al. | 356/326 |
| 2006/0088939 A1 * | 4/2006 | Rajendram | 436/31 |

FOREIGN PATENT DOCUMENTS

WO    WO 2004/079365 A    9/2004

OTHER PUBLICATIONS

Chang, C. W., et al., "Near-infrared reflectance spectroscopy-principal components regression analyses of soil properties" Soil Science Society of America Journal Mar.-Apr. 2001, vol. 65, No. 2, pp. 480-490, see entire document.
Malley, D.F., et al., "Rapid analysis of hog manure and manure-amended soils using near infrared spectroscopy" Soil Science Society of America Journal Sep.-Oct. 2002, vol. 66, No. 5, pp. 1677-1686, see near infrared spectroscopy section on p. 1679.
Russell, C.A., et al., "The potential of NIR spectroscopy to predict nitrogen mineraltization in rice soils" Plant and Soil 2002, vol. 247, pp. 243-252, see soil NIR calibration section on pp. 245-246.
van Groenigen, J.W., et al., "NIR and DRIFT-MIR spectrometry of soils of predicting soil and crop parameteres in a flooded field" Plant and Soil 2003, vol. 250, pp. 155-165, see entire document.

* cited by examiner

*Primary Examiner*—David P Porta
*Assistant Examiner*—Faye Boosalis
(74) *Attorney, Agent, or Firm*—Thomas, Kayden, Horstemeyer & Risley, LLP

(57) ABSTRACT

Methods and systems related to soil testing are disclosed. One exemplary embodiment of a system of the present disclosure includes a calibrated near-infrared (NIR) spectrophotometer and a soil sample with an unknown value of at least one of pH and b disposed in proximity to the calibrated NIR spectrophotometer, the NIR spectrophotometer configured to produce a spectrum from a reading of the sample.

15 Claims, 1 Drawing Sheet

SYSTEMS AND METHOD FOR PREDICTING THE LIME REQUIREMENT IN SOILS

CROSS-REFERENCE TO RELATED APPLICATIONS

This U.S. national phase application claims priority to PCT application no. PCT/US05/45379, international filing date 15 Dec. 2005, which claims priority to U.S. provisional application Ser. No. 60/636,784, filing date 16 Dec. 2004, both of which are entirely incorporated herein by reference.

TECHNICAL FIELD

The present disclosure is generally related to systems and methods for testing soil, and more particularly, to systems and methods for predicting the lime requirement in soils.

BACKGROUND

The application of lime in order to correct soil pH has been shown to be agronomically feasible in many cropping situations. Lime application, however, is only desired in low pH soils, and may even be detrimental if applied to high pH soils. Consequently, it is desirable to accurately assess the spatial variability of soil pH and lime requirements.

Buffer methods are typically used by soil testing laboratories in the U.S. for the prediction of the LR of acid soils. For example, the AE buffer procedure (Adams F., and C. E. Evans, 1962. A rapid method for measuring the lime requirement of Red-Yellow Podzolic soils. Soil Sci. Am. Proc. 26:355-357) is used widely in the southeastern and mid-Atlantic regions of the U.S., and the SMP buffer (Shoemaker H. E., E. O. McLean, and P. F. Pratt, 1961. Buffer methods for determination of lime requirements of soils with appreciable amount of exchangeable aluminum. Soil Sci. Soc. Am. Proc. 25:274-277) is widely used in the Midwest regions (Sims, J. T., 1996. Lime requirement. p. 491-515. In D. L. Sparks (ed.) Methods of soil analysis. Part 3. SSSA Book Series Book Series No. 5 SSSA, Madison, Wis.). The accuracy of these buffers has been widely studied (Follett, R. H. and R. F. Follett, 1980, Strengths and weaknesses of soil testing in determining lime requirements for soils. p. 40-51. In Proc. of the Natl. Conf. on Agric. Limestone 16-18 Oct. 1980. Tennessee Valley Authority, National Fertilizer Development Center, Muscle Shoals, Ala.; Tran, T. S., and W. van Lierop, 1981. Evaluation and improvement of buffer-pH lime requirement methods. Soil Scci. 131: 178-188; Alabi K. E., R. C. Sorensen, D. Knudsen, and G. W. Rehm. 1986. Comparison of several lime requirement methods on coarse-textured soils of Northeastern Nebraska. Soil Sci. Soc. Am. J. 50:937-941). A recent concern about buffers is the potential toxicity of their components. Both the AE and SMP buffers contain p-nitrophenol, a potentially toxic compound.

A possible alternative method for determining the LR of acid soils is by direct titration with a base, although these methods are time-consuming and would need to be simplified for routine use. Dunn studied direct titration to predict the LR of acid soils and focused on the time to reach equilibrium for the reaction between the added base and soil acids. Dunn, L. E. 1943. Lime requirement determination of soils by means of titration curves. Soil Sci. 56:341-351. Dunn found that 4 days were needed for pH values to reach equilibrium when a 0.022 M $Ca(OH)_2$ solution was added to acid soils. Dunn also discovered that shaking affected the time required for soil pH values to reach equilibrium. Dunn reported that a constant pH was reached within 8 hours when the soil suspensions were mixed by shaking, whereas 4 days were required for the suspensions to obtain a stable pH without shaking. Finally, Dunn suggested a direct titration method for LR by incorporating acid soils with different rates of 0.022 M $Ca(OH)_2$ for 4 days. The $Ca(OH)_2$ titration method suggested by Dunn for measuring the LR was widely accepted as a reliable method for evaluating buffer methods that were developed for estimating the LR (Follett and Follett, 1980; Alabi et al., 1986; McConnell, J. S., J. T. Gilmour, R. E. Baser, and B. S. Frizzell. 1991. Lime requirement of acid soils of Arkansas. Arkansas Exp. Stn. Spec. Rep. 150. Arkansas Agric. Exp. Stn., Fayetteville; Owusu-Bennoah, E. Acquaye, D. K. Mahamah, T. 1995. Comparative study of selected lime requirement methods for some acid Ghanaian soils. Commun. Soil Sci. Plant Analy. 26:937-950). However, Dunn's method was also considered to be a time-consuming procedure and not suitable for routine use in soil testing laboratories.

Many studies focused on the titration curve itself. Magdoff et al. concluded that the relationship between pH and $OH^-$ added is nearly linear within the pH range of most agricultural soils (4.5-6.5). Magdoff, F. R., and R. J. Bartlett. 1985. Soil pH buffering revisited. Soil Sci. Soc. Am. Proc. 49:145-148. Weaver et al. also reported a linear relationship between pH and base added for a series of Georgia soils. Weaver, A. R. D. E. Kissel, F. Chen, L. T. West, W. Adkins, D. Rickman, and J. C. Luvall. 2004. Mapping soil pH buffering capacity of selected fields in the coastal plain. Soil Sci. Soc. Am. J. 68:662-668. The slope of the linear relationship of pH versus $OH^-$ added is also a fundamental property of the soil, which could possibly be determined by other methodologies.

SUMMARY

Briefly described, embodiments of the present disclosure include methods and systems related to soil testing. Specifically, one exemplary method of the present disclosure includes individually scanning a plurality of preselected soil samples with a near-infrared (NIR) spectrophotometer and producing NIR spectra for each preselected soil sample; measuring an initial pH of each preselected soil sample; correlating the initial pH of each preselected soil sample with each NIR spectrum produced for the respective preselected soil sample; determining the buffering capacity (b) of each preselected soil sample based on each spectrum, whereby the NIR spectrophotometer is calibrated with the measured spectra; scanning and producing a NIR spectrum for a soil sample with an unknown value of at least one of pH and b with the calibrated NIR spectrophotometer; and producing a value of at least one of pH and b for the unknown sample based on the spectra used to calibrate the NIR spectrophotometer.

The systems included in the present disclosure relate to testing soils with an NIR spectrophotometer in order to determine certain properties about a soil sample. For example, one exemplary embodiment of a system of the present disclosure includes a calibrated near-infrared (NIR) spectrophotometer; and a soil sample with an unknown value of at least one of pH and b disposed in proximity to the calibrated NIR spectrophotometer, the NIR spectrophotometer configured to produce a spectrum from a reading of the sample.

Other systems, methods, features, and advantages of the present disclosure will be or will become apparent to one with skill in the art upon examination of the following drawing and detailed description. It is intended that all such additional systems, methods, features, and advantages be included within this description, be within the scope of the present disclosure, and be protected by the accompanying claims.

BRIEF DESCRIPTION OF THE DRAWING

Aspects of the disclosed systems and methods can be better understood with reference to the following drawing.

DETAILED DESCRIPTION

Figure 1:
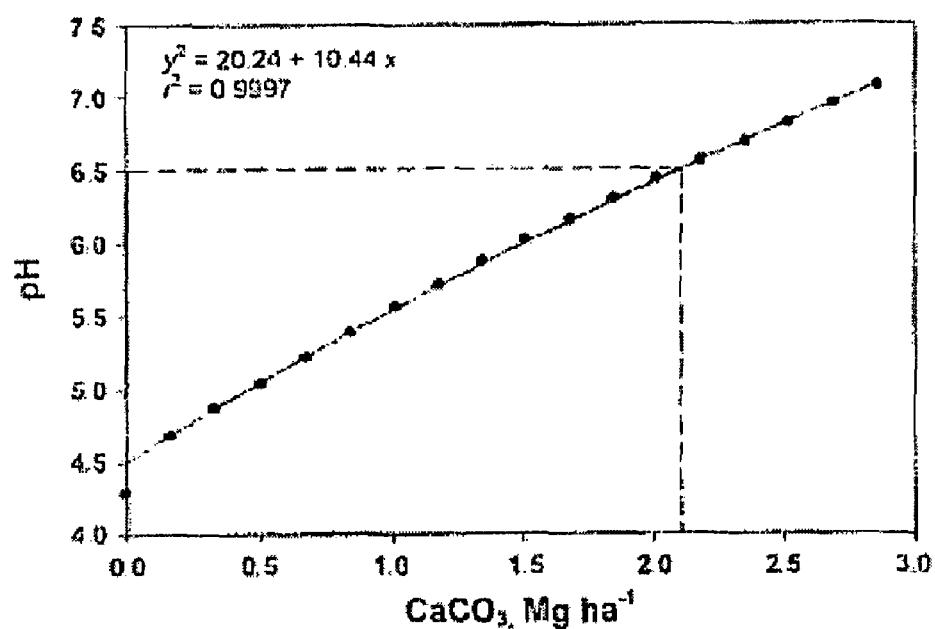
FIG. 1 is an exemplary graph illustrating a titration curve to pH of a 7 for a soil sample.

The technology relates to systems and methods for predicting the lime (i.e., calcium carbonate) requirement in soil. Being able to predict the lime requirement for soil is important for rendering soils less acidic, or even neutral. Acidic soils that have not been properly limed affect root growth and, ultimately, crop yield. The lime requirement of soil is based on its pH, which can vary by as much as 2 pH points across one field.

It has been discovered that measurement of only a few data points of pH versus OH— added, followed by linear extrapolation to the target pH, gave lime requirements very close to those determined from the complete titration curve. With the slope of the linear relationship of pH versus $OH^-$ being a fundamental property of the soil, it has also been discovered that lime requirements can be determined by other methodologies, such as Near-Infrared Reflectance (NIR) spectroscopy.

The disclosed technology provides fundamental laboratory protocols and mathematical relationships that make possible the use of NIR spectroscopy for estimating two fundamental soil properties, soil pH and soil $H^+$ ion buffering capacity. With a reasonably accurate estimate of both, it is possible to calculate the amount of lime needed by the soil to raise pH to the desired target value by using the following relationship:

$$\text{Lime needed} = 1/b \times (\text{target pH} - \text{measured pH}) \quad (1),$$

where b is the soil's $H^+$ ion buffering capacity, determined by titration with calcium hydroxide. It has been determined from practicing the disclosed methods on a wide range of soil types that the pH is a function of the calcium hydroxide added during titration and the relationship between the pH and calcium chloride can be correlated to a linear equation. The linear equation (2) is as follows:

$$\text{pH} = \text{initial pH} + b \times \text{calcium hydroxide added} \quad (2),$$

where the value of b is the slope. For simplicity, the units of calcium hydroxide may be expressed as the chemically equivalent amounts of calcium carbonate, the typical liming agent used on farms. The units of b would then be expressed as $\Delta$ pH/$\Delta$ calcium carbonate added. When used in equation (1), the units of pH cancel and the result is the pounds of calcium carbonate to be applied per acre. The value of b can be modified for plow layer depth (selected by the farmer) and soil bulk density (from soil's databases) and limestone quality in order to modify the laboratory-determined value of b.

It has been determined from the disclosed methods that both soil pH and the soil's $H^+$ ion buffering capacity are statistically related to NIR spectroscopy scans of a group of over 200 soil types. As a result, both soil properties can be predicted from scanning soils with NIR spectroscopy equipment. The values of initial pH and b can then be used in equation (1) to calculate the lime needed for a soil.

The disclosed methods include first calibrating the NIR spectrophotometer by scanning and producing spectra for a number of soil samples (e.g., about 49), each with known (and different) pH and buffering capacity (b). The scans of the soil samples with known pH's and b's are used to derive equations that are able to calculate pH's and b's based on the spectra of other (unknown) soil samples.

The pH and b of the initial, calibration (e.g., the initial 49) soil samples are obtained in the following novel manner for each soil sample. The initial pH of soil sample ($pH_1$) is first taken using a standard ion-selective electrode. An exemplary soil/water suspension sample can be 20 grams of soil mixed with 20 mL of water (i.e., 1:1).

Optionally, the ionic strength can be controlled by addition of an aliquot of calcium chloride to each soil sample. It has been demonstrated in the past that the ionic strength of the same soil sample can be affected by, for example, amount of rainfall, amount/timing of fertilizer application, temperature conditions, degradation of organic matter in the soils by organisms, etc. In order to normalize all samples to eliminate ionic strength as a factor in $pH_1$, the soil samples can be tested in, for example, 0.01M $CaCl_2$ for $pH_1$.

If $pH_1$ of the soil is below a predetermined value (e.g., 5.4) at which the soil conditions are unfavorable for growth, a known aliquot of a basic solution is added. The predetermined value at which the soil conditions are unfavorable for growth will vary depending on crop. The known aliquot of the basic solution can be, for example, 2 mL of saturated $Ca(OH)_2$ for the 20 g soil sample. After the aliquot of $Ca(OH)_2$ has been added with stirring, and after a specific amount of time has elapsed (e.g., 30 minutes), the pH is measured again. At this point, the buffer solution has increased the pH of the initially acidic soil to a second pH ($pH_2$). Due to differences in buffering capacities of the various soil samples, $pH_2$ of the individual soil samples can vary tremendously from each other, even within the same field or region. The buffering capacity, b, is then calculated according to the following formula:

$$b = \Delta pH / \Delta \, CaCO_3 \, (\text{per kg of soil}) \quad (3),$$

where $\Delta CaCO_3$ is the amount of $Ca(OH)_2$ added (expressed as the equivalent amount of $CaCO_3$), and $\Delta pH$ is ($pH_2 - pH_1$).

The graph of FIG. 1 represents the complete titration curve to pH 7 for a soil sample, using a 30-minute time interval between additions of $Ca(OH)_2$. It should be noted that if $CaCl_2$ is not used to account for ionic strength, then one or two more aliquots of base may be needed to generate a more accurate titration curve, where b represents the slope of the titration curve, because the first data point on the y-axis is depressed. Thus, the novel laboratory method uses only enough titration data points to establish the slope for the linear equation for calculation of the lime requirement, making it feasible for highly accurate (due to number of samples that can easily be tested), yet routine laboratory use.

Many soil samples should be tested as feasible for a given geographic region to calibrate the NIR because the buffering capacity for soil samples can vary as much as eight- or ten-fold within a soil geographic region. For example, in 49 soils samples taken in Georgia, there existed an eight-fold difference in b. Once $pH_1$ and b have been determined for a sufficient number of soil samples, a NIR spectrophotometer can be calibrated as noted above. Once calibrated, the NIR measures the soil independent of soil color, type, or texture.

Also included in the method of the disclosed technology is taking NIR spectral data from a field via a "ruggedized," calibrated NIR spectrophotometer. The ruggedized NIR spectrophotometer is built to withstand the conditions typically present in a field that might otherwise be adverse to operation of a sensitive detection instrument, such as for example, but not limited to, humidity, dust, wind, jostling, vibrations, and temperature extremes.

Based on the calibration, a software program can convert the NIR spectral data into pH and b determinations for every scan taken. The software can be linked with global positioning system (GPS) software, thus "mapping" the field in very discrete and small areas according to pH and b. The values of pH and b, along with a farmer's desired pH, can be inserted in Equation 1 above to arrive at a lime requirement for every discrete sector of a given field.

It should be emphasized that the above-described embodiments of the devices, systems, and methods are merely possible examples of implementations of the devices, systems, and methods, and are merely set forth for a clear understanding of the principles set forth herein. Many variations and modifications may be made to the devices, systems, and methods disclosed herein without departing substantially from the spirit and principles of the disclosure. All such modifications and variations are intended to be included herein within the scope of this disclosure and protected by the following claims.

At least the following is claimed:

1. A method of testing a soil sample with unknown pH and/or buffering capacity (b), the method comprising:
   producing near-infrared (NIR) spectra for a plurality of preselected soil samples;
   measuring an initial pH ($pH_1$) of each preselected soil sample;
   determining b of each preselected soil sample;
   correlating the initial pH and buffering capacity (b) of each preselected soil sample with each NIR spectrum produced for the respective preselected soil sample to produce a calibration curve;
   producing a NIR spectrum for a soil sample with an unknown value of at least one of pH and b; and
   producing a value of at least one of pH and b for the unknown sample based on the calibration curve.

2. The method of claim 1, wherein the step of determining the buffering capacity of each preselected soil sample comprises:
   (i) adding a known aliquot of a solution with a basic pH to the soil sample;
   (ii) determining the pH of the soil sample after the basic solution is added ($pH_2$);
   (iii) determining the buffering capacity of each soil sample according to the following formula: b = $\Delta pH/\Delta CaCO_3$ (per kg of soil), wherein $\Delta CaCO_3$ is the amount of $Ca(OH)_2$ added (expressed as the equivalent amount of $CaCO_3$), and $\Delta pH$ is ($pH_2$-$pH_1$);
   (iv) repeating steps (ii)-(iv); and
   (v) calculating an average b, based on each b value determined in step (iv).

3. The method of claim 2, further comprising the step of determining whether the soil sample is below a predetermined value of pH at which soil conditions are unfavorable for growth.

4. The method of claim 3, wherein the solid conditions unfavorable for growth comprise having a pH less than or equal to about 5.4.

5. The method of claim 2, wherein repeating steps (ii)-(iv) comprises a multitude of repetitions.

6. The method of claim 2, wherein repeating steps (ii)-(iv) comprises one repetition.

7. The method of claim 2, wherein repeating steps (ii)-(iv) comprises two repetitions.

8. The method of claim 1, wherein the step of producing a value of at least one of pH and b for the unknown sample based on the calibration curve comprises producing a value of at least one of pH and b for the unknown sample via data stored in a computer-readable medium.

9. The method of claim 2, wherein the step of producing a value of at least one of pH and b for the unknown sample based on the calibration curve comprises producing a value of at least one of pH and b for the unknown sample via data stored in a computer-readable medium.

10. The method of claim 1, further comprising determining a target pH for the soil sample having an unknown value selected from at least one of pH and b.

11. The method of claim 1, further comprising calculating the lime requirement of a soil sample based on the following formula: Lime needed=1/b×(target pH−measured pH).

12. A system for testing a soil sample with unknown pH and/or buffering capacity (b), the system comprising:
   a calibrated near-infrared (NIR) spectrophotometer calibrated using an initial pH and a determined value of b for each of a plurality of preselected soil samples; and
   a soil sample with an unknown value of at least one of pH and b disposed in proximity to the calibrated NIR spectrophotometer, whereby the NIR spectrophotometer can produce a spectrum of a reading of the sample;
   wherein the value of at least one of pH and b is determined for the unknown soil sample based on the spectrum produced.

13. The system of claim 12, wherein the NIR spectrophotometer is calibrated by producing near-infrared (NIR) spectra for a plurality of preselected soil samples, measuring an initial pH ($pH_1$) of each preselected soil sample, correlating the initial pH of each preselected soil sample with each NIR spectrum produced for the respective preselected soil sample, and determining buffering capacity (b) of each preselected soil sample based on each spectrum, to produce a calibration curve.

14. The system of claim 12, wherein determining the buffering capacity (b) of each preselected soil sample comprises:
   (i) adding a known aliquot of a solution with a basic pH to the soil sample;
   (ii) determining the pH of the soil sample after the basic solution is added ($pH_2$)
   (iii) determining the buffering capacity of each soil sample according to the following formula: b = $\Delta pH/\Delta CaCO_3$ (per kg of soil), wherein $\Delta CaCO_3$ is the amount of $Ca(OH)_2$ added (expressed as the equivalent amount of $CaCO_3$), and $\Delta pH$ is ($pH_2$-$pH_1$);
   (iv) repeating steps (ii)-(iv); and
   (v) calculating an average b, based on each b value determined in step (iv)

15. The system of claim 12, further comprising a computer-readable medium that determines the value of at least one of pH and b for the unknown soil sample based on the spectrum produced by the calibrated NIR spectrophotometer.

* * * * *

UNITED STATES PATENT AND TRADEMARK OFFICE
CERTIFICATE OF CORRECTION

| | | |
|---|---|---|
| PATENT NO. | : 7,679,058 B2 | Page 1 of 1 |
| APPLICATION NO. | : 11/792807 | |
| DATED | : March 16, 2010 | |
| INVENTOR(S) | : Kissel et al. | |

It is certified that error appears in the above-identified patent and that said Letters Patent is hereby corrected as shown below:

Please insert in the "Government Interests" section:

--*STATEMENT REGARDING FEDERALLY SPONSORSED RESEARCH OR DEVELOPMENT*

*This invention was made with government support under Grant No. 2000-31100-00867 awarded by the USDA/CSREES. The U.S. government has certain rights in the invention.*--

Signed and Sealed this

Eleventh Day of May, 2010

David J. Kappos
*Director of the United States Patent and Trademark Office*